United States Patent
Demirtas

(10) Patent No.: US 10,925,645 B2
(45) Date of Patent: Feb. 23, 2021

(54) EXTERNAL FIXATOR

(71) Applicant: Ahmet Mehmet Demirtas, Ankara (TR)

(72) Inventor: Ahmet Mehmet Demirtas, Ankara (TR)

(*) Notice: Subject to any disclaimer, the term of this patent is extended or adjusted under 35 U.S.C. 154(b) by 59 days.

(21) Appl. No.: 16/306,613

(22) PCT Filed: Jun. 3, 2016

(86) PCT No.: PCT/TR2016/050164
§ 371 (c)(1),
(2) Date: Dec. 3, 2018

(87) PCT Pub. No.: WO2017/209710
PCT Pub. Date: Dec. 7, 2017

(65) Prior Publication Data
US 2019/0223915 A1    Jul. 25, 2019

(51) Int. Cl.
*A61B 17/64* (2006.01)
(52) U.S. Cl.
CPC ...... *A61B 17/6425* (2013.01); *A61B 17/6416* (2013.01)
(58) Field of Classification Search
CPC .................................................. A61B 17/6425
See application file for complete search history.

(56) References Cited

U.S. PATENT DOCUMENTS

| | | | |
|---|---|---|---|
| 5,545,162 A | 8/1996 | Huebner | |
| 6,709,433 B1 | 3/2004 | Schoenefeld | |
| 2002/0004659 A1* | 1/2002 | Boudard | A61B 17/60 606/54 |
| 2003/0109879 A1 | 6/2003 | Orsak | |
| 2004/0181221 A1* | 9/2004 | Huebner | A61B 17/6425 606/59 |
| 2004/0249375 A1 | 12/2004 | Agee et al. | |
| 2009/0222006 A1* | 9/2009 | Allison | A61B 17/60 606/54 |
| 2011/0144643 A1* | 6/2011 | Lorenz | A61B 17/6416 606/59 |
| 2012/0259344 A1* | 10/2012 | Johnston, Jr. | A61B 17/66 606/105 |
| 2016/0030028 A1* | 2/2016 | Van Dyke | A61B 17/025 606/90 |

FOREIGN PATENT DOCUMENTS

FR    2808181 A1    11/2001
FR    2824468 A1    11/2002

* cited by examiner

*Primary Examiner* — Tessa M Matthews
(74) *Attorney, Agent, or Firm* — Bayramoglu Law Offices LLC

(57) ABSTRACT

The present invention relates to reduction and fixation of bone fractures distal radius and wrist. The invention enables to mobilise the distal fragment in 3 planes and also to correct rotational deformity. The object of the present invention is to realize an external fixator which enables to reduce a fracture and at the desired position and fix the fracture. In case of unsuccessful reduction attempt for the second trial there is no need to dismount the fixator. Another object of the present invention is to realize an external fixator which enables to reduce a fracture in 3 dimensions and to correct the rotational deformity in a preferred degree. Another object of the present invention is to realize an external fixator which can practically be mounted to malunion zone and can be used for reducing in corrective osteotomy operations.

10 Claims, 6 Drawing Sheets

EXTERNAL FIXATOR

CROSS REFERENCE TO RELATED APPLICATIONS

This application is the national phase entry of International Application No. PCT/TR2016/050164, filed on Jun. 3, 2016, and the entire contents of which are incorporated herein by reference.

TECHNICAL FIELD

The present invention relates to reduction and fixation of bone fractures distal radius and wrist. The invention enables to mobilise the distal fragment in 3 planes and also to correct rotational deformity.

BACKGROUND

Distal radius fracture is one the most common injuries of upper extremity. Many people suffer from this injury every year and are enabled to use their wrists. Distal radius plates and external fixators are the devices used for fixing this fracture. New generation plates have variable angle locking facilities as this increases the stability External fixation can basically be described as fastening two separate parts of the fractured bone with screws or wires which are put through the holes on the units forming the external fixator.

External fixators are used to maintain a reduced bone in a stable state. There is no chance to change the stable state provided by the external fixator, once the bone is fixed. If a fracture is reduced inaccurately in a bad position the fixator has to be removed and fracture has to be reduced again.

The United States patent document no U.S. Pat. No. 5,545,162 discloses a bone fixator for repairing fractures of the distal radius and wrist. It includes, in the preferred embodiment, at least two generally parallel spaced-apart elongate distal mounting pins with lower ends for mounting in the metacarpal bone and at least two generally parallel spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. The fixator further includes a proximal pin mounting block for securing the radial pins and an elongate medial assembly of adjustable length. The medial assembly is pivotally connected at one end to the pin mounting block for independent pivotal motion about an axis generally parallel to the elongate axes of the proximal mounting pins and coupled at the opposed end through a ball joint to the distal member.

The United States patent document no U.S. Pat. No. 6,709,433 discloses an external bridging/non-bridging bone fixation device including at least a first member and a second member. The first member is implanted substantially permanently on an arm bone during an entire healing process. Whereas the second member is adapted to be substantially temporarily implanted and affixed between the first member and a metacarpal of the associated hand. The second member may be a singular rigid piece or may be formed of several modular pieces affixed together. In particular, the second member may be hinged to allow for an offset or angled implantation. Also, the second member may include a plurality of pieces that are rigidly held together after implantation to allow for high selectivity by a physician. The bridging/non-bridging bone fixation device allows for a bridging adaptation during an initial portion of healing and a non-bridging adaptation during the extended healing process to reduce the possibility of stiffness and plaques due to prolonged periods of immobility.

The United States patent document no US2003109879 discloses an external fixator for fixating fractures provides an elongated support rod that includes proximal and distal rod sections. Fixation pins are provided for engaging the patient's bone tissue on opposite sides of a fracture. Clamps are rotatably supported upon the proximal rod section and distal rod section, each of the clamps being movable in rotational fashion both with respect to the rod and with respect to the pins. At least one of the clamps has articulating portions that rotate and angulate relative to one another so that total adjustment is provided between the rod and the pins. The articulating portion can be rigidified using one set fitting or set screw.

The United States patent document no US2004249375 discloses an external fixator that includes mounting structures attachable to the radius at a site proximal to the fracture and to a metacarpal, joined by a connector whose length is capable of both gross adjustment and precision adjustment, each mounting structure providing degrees of freedom independently of the connector length, the mounting structure at the radius end providing independent degrees of freedom for rotation around a proximal-distal axis and for rotation about an axis transverse to an axis parallel to the proximal-distal axis.

SUMMARY

The object of the present invention is to realize an external fixator which enables to reduce a fracture and at the desired position and fix the fracture. In case of unsuccessful reduction attempt for the second trial there is no need to dismount the fixator.

Another object of the present invention is to realize an external fixator which enables to reduce a fracture in 3 dimensions and to correct the rotational deformity in a preferred degree.

Another object of the present invention is to realize an external fixator which can practically be mounted to malunion zone and can be used for reducing in corrective osteotomy operations.

BRIEF DESCRIPTION OF THE DRAWINGS

An external fixator realized to fulfil the objective of the present invention is illustrated in the accompanying figures, in which.

DETAILED DESCRIPTION OF THE EMBODIMENTS

Figure 1:
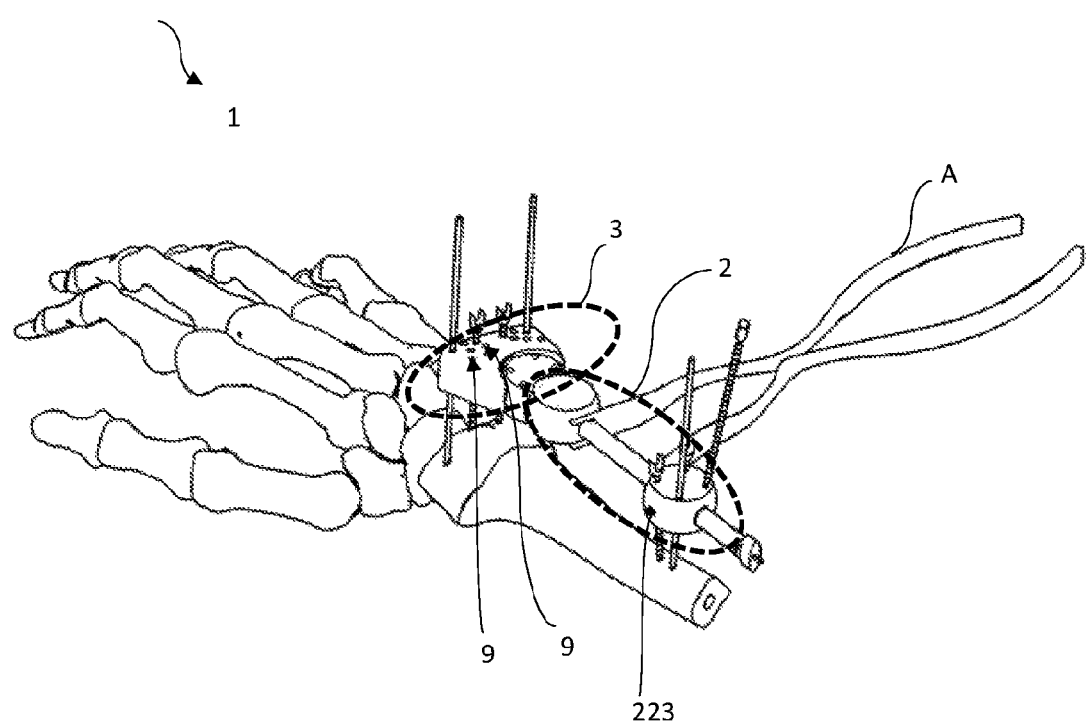
FIG. 1 is a view of external fixator while being mounted on a fracture zone
Figure 2:
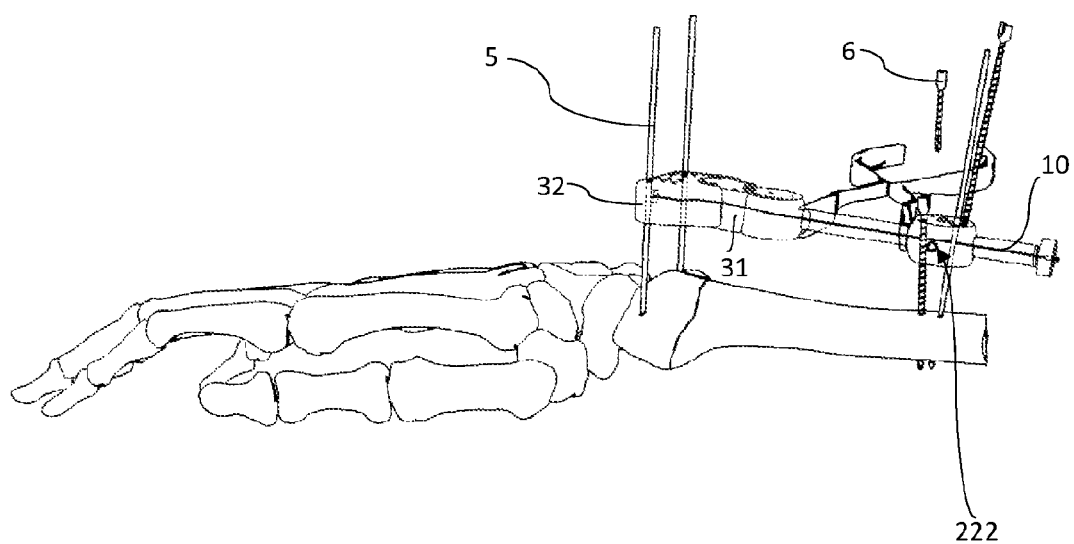
FIG. 2 is another view of external fixator while being mounted on a fracture zone
Figure 3:
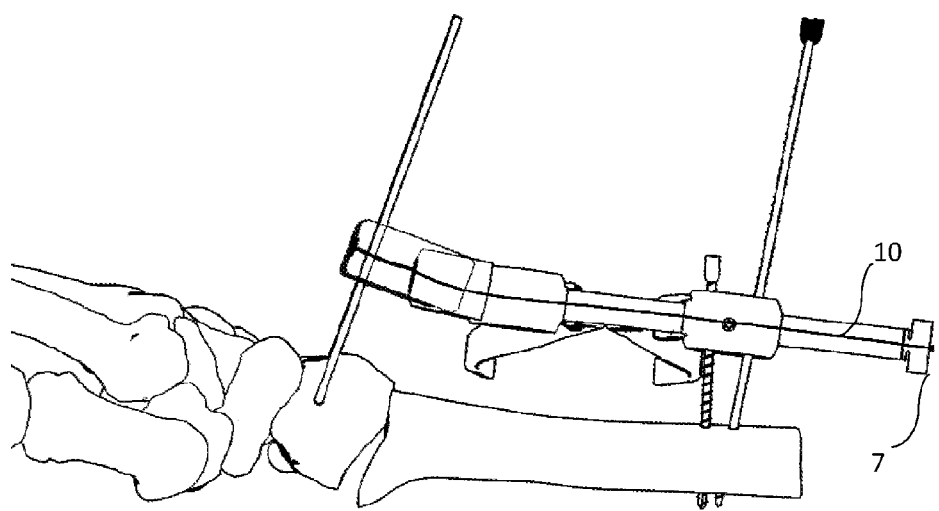
FIG. 3 is another view of external fixator while being mounted on a fracture zone
Figure 4:
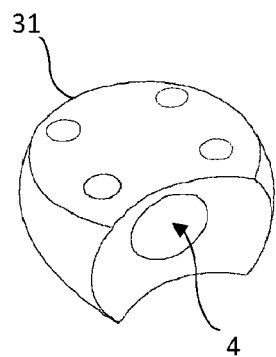
FIG. 4 is a view of joint unit
Figure 5:
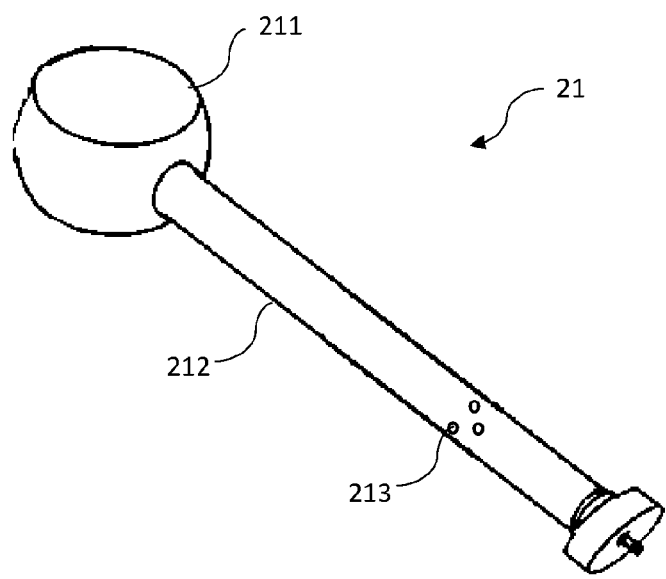
FIG. 5 is a view of rod
Figure 6:
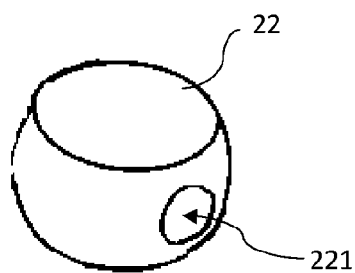
FIG. 6 is a view of slider unit
Figure 7:
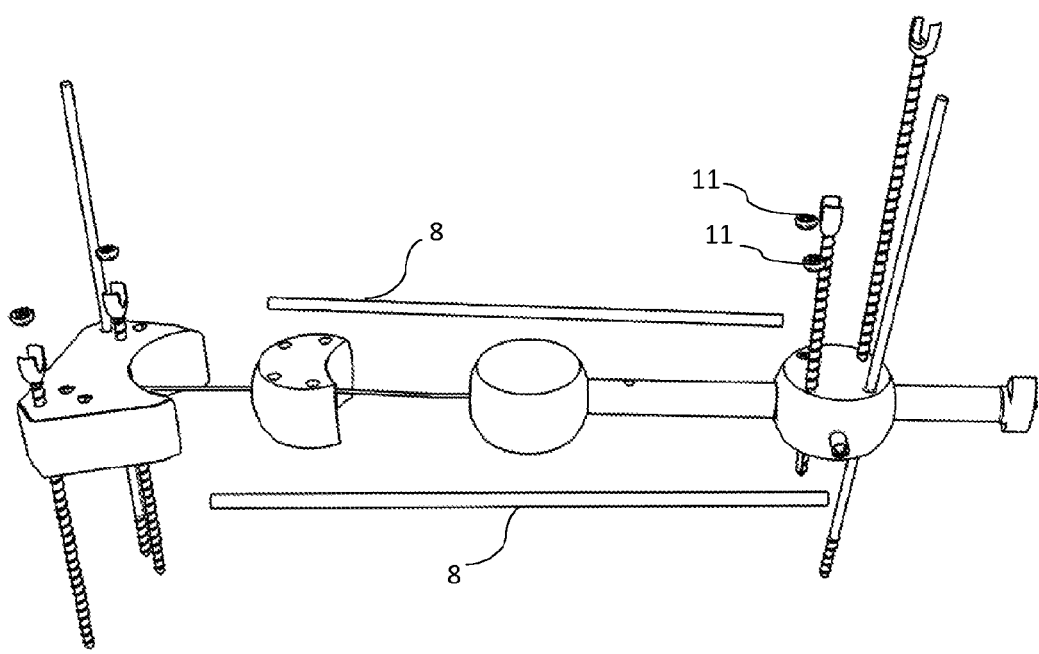
FIG. 7 is an exploded view of external fixator
Figure 8:
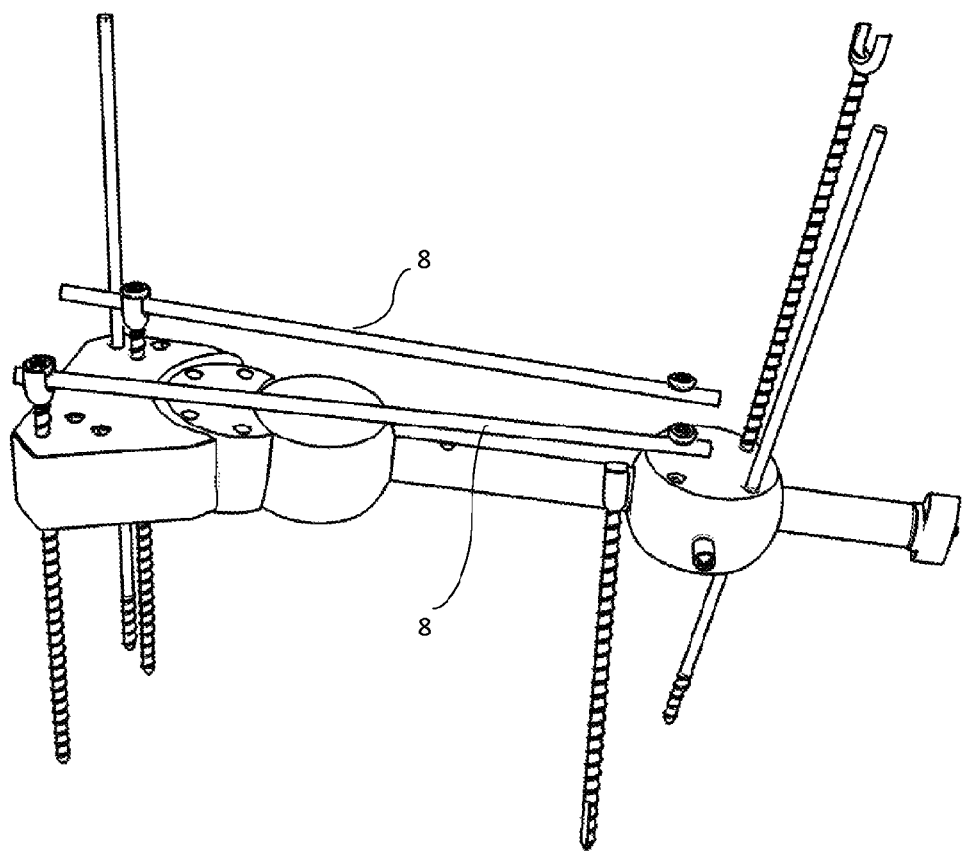
FIG. 8 is a view of external fixator The parts illustrated in the figures are individually numbered where the numbers refer to the following:
1. External fixator
2. Proximal part
   21. Rod
      211. Knob
      212. Stick
      213. Rotational adjustment reference hole
   22. Slider unit
      221. Slider hole
      222. Rotational fixation hole
      224. Rotational fixation screw
3. Distal part
   31. Joint unit
   32. Movable unit
4. Conic hole
5. Affixation wire
6. Tulip head
7. Locker
8. Bar
9. Affixation hole
10. Main wire
11. Nut
A. Distractor

The external fixator (1) comprises
a proximal part (2) adapted to be affixed to proximal radius bone, wherein the proximal part (2) comprising
   a rod (21) which have a knob (211) in the form of a truncated sphere with a conic hole (4) inside and a stick (212),
   a slider unit (22) enabling the stick (212) slide through a slider hole (221),
a distal part (3) adapted to be affixed to distal fracture fragment or metacarpal bone, wherein the distal part (3) comprising
   a movable unit (32), with a conic hole (4) inside, which have a cavity that convex surface of the truncated sphere formed knob (211) fits into concave surface resulting from the cavity,
a main wire (10) inside the stick (212) which stretches between a locker (7) and the movable unit (32), moves as the movable unit (32) moves,
the conic holes (4) which limit movement of the main wire (10), are located that inside the knob (211) and inside the movable unit (32),
at least one affixation hole (9) which is located on the slider unit (9) for affixing proximal part (2) to the proximal radius and on the movable unit (32) for affixing distal part (3) to the metacarpal bone via affixation wires (5).

The external fixator (1) has a proximal part (2) that is parallelly or almost parallelly affixed to the proximal radius bone. This affixation is realized via affixation wires (5) which pass through affixation holes (9) on the slider unit (9) and drill into the proximal radius bone.

Distal part (3) is affixed to the distal fracture fragment or to the metacarpal bone via affixation wires (5) which pass through affixation holes (9) on the movable unit (32) and drills into the bone.

Proximal and distal parts (2),(3) which are affixed to two separate parts of the fracture, remain together by means of the main wire (10). The main wire (10) is stretched between the locker (7) and the movable unit (32). The stretched main wire (10) extends longitudinally in the stick (212) and one end of the main wire (10) is welded to the movable unit (32) from top of the conic hole (4) in the movable unit (32) while the other end of it is welded to the locker (7). Thus, "tension fixation" is achieved.

Being affixed to the proximal radius bone, the slider unit (22) enables the stick (212) to slide in the slider hole (221). Sliding movement of the stick (212) on the distal direction is limited by the locker (7) while the knob (211) limits the movement on the opposite direction. These limitations are realized by the means of the sizes of the both locker (7) and knob (211) as they are bigger than the cross section of the slider hole (221).

Sliding movement—on the distal direction in the normal reduction operation—of the stick (212) is provided by the usage of the affixation wires (5) on the movable unit (32) like a joystick. This movement is available on the axis of the main wire (10). The movable unit (32) also moves on the same axis as the stick moves (212).

Once the longitudinal length has restored, slider (22) is fixed to the stick (212) via affixation wires (5). When the first movement of the movable unit (32) is being provided by the affixation wires (5), a distractor may be used as an assistant to the sliding movement as it placed between the knob (211) and the slider unit (22) and force them to move on the opposite directions to maintain longitudinal reduction.

The joystick-like usage also provides a second movement of the movable unit (32) dependent on a space that two conic holes (4) form, as the base of the conic hole (4) inside the knob (211) overlaps the base of the conic hole (4) inside the movable unit (32) at the zero point (initial or non-used position) of the external fixator (1). The space formed and bordered by the volume of said two conic holes (4) limits the movement of the main wire (10) thus the movement of the movable unit (32) is limited by the said space. The second movement is a resultant of a two rotational movements on two orthogonal axis as the knob (211), which works as a pivot for the movable unit (32), has a truncated sphere form. This movement enables distal fragment to move in 3 dimensions, so rotational corrections of the fracture can be done.

In an another embodiment of the invention, external fixator (1) may also comprise,—at least one joint unit (31) in the form of a truncated sphere which has an additional cavity and is located between movable unit (32) and the knob (211), that convex surface of the knob (211) fits into concave surface resulting from the cavity wherein concave surface of the joint unit (31) fits into convex surface of the movable unit (32).

The joint unit (31) has two conic holes (4) that base of one of them is overlaps with the base of the conic hole (4) inside the movable unit (32) and base of the other one overlaps with the base of the conic hole (4) inside the knob (211) at the zero point (initial or non-used position) of the external fixator (1).

In an another embodiment of the invention, external fixator (1) may also comprise,—at least a bar (8) located between tulip heads (6) and nuts (11), for maintaining the two fastened parts of the fractured bone in a stable state with both proximal and distal parts (2), (3).

After the affixation wires (5) on the movable unit (32) are used to reduce the fracture, at least one bar (8) is used to maintain external fixator (1) and so the reduced bone in a stable state. One bar's (8) two far ends is placed in two tulip heads (6) which are on top of affixation wires (5) that the bar (8) is located in a parallel or almost parallel position to the proximal radius bone. Said bar (8) is tamped in the tulip heads (6) by a nut (11) as inner part of the tulip heads (6) are grooved. Bars (8) are used with the purpose of maintaining durability of the fixator (1) in case of affixation wires (5) may fail in time.

In an another embodiment of the invention, external fixator (1) may also comprise,—rotational adjustment reference holes (213) located on the stick (212).

Rotational adjustment reference holes (213) are located on the stick (212) with a preferred degree in order to be a reference point for the rotational adjustment of the fracture. For example, one rotational adjustment reference hole (213) is located on the preferred reference point of the external fixator when there is no rotational adjustment is performed on the fracture. And the second rotational adjustment reference hole (213) is located as it will be on the reference point after a rotational adjustment is performed. Let's say there is a 15 angle between first and the second rotational adjustment reference holes (213), the second one is the reference for a 15 rotational adjustment. Thus the operator can be aware of how many degrees of rotational adjustment is performed.

In a preferred embodiment of the invention, the slider unit (22) may have a rotational fixation hole (222) allowing a rotational fixation screw (223) to get through and touch to the stick (212) for stabilizing the slider unit on the stick (212) on a arranged rotational position.

In a preferred embodiment of the invention, the affixation wires (5) may be threaded Kirschner wires, non-threaded Kirschner wires or tulip heads (6) with nuts (11).

Within the scope of these basic concepts, it is possible to develop a wide variety of embodiments of the inventive external fixator (1). The invention cannot be limited to the examples described herein; it is essentially according to the claims.

What is claimed is:

1. An external fixator comprising:
   a proximal part adapted to be affixed to a proximal radius bone, and
   a distal part adapted to be affixed to a distal fracture fragment or a metacarpal bone;
   wherein,
   the proximal part comprises
      a rod having a knob in a form of a truncated sphere with a first conic hole inside the knob and a stick, and
      a slider unit configured to make the stick slide through a slider hole;
   the distal part comprises
      a movable unit with a second conic hole inside the movable unit, the movable unit having a first cavity;
   wherein, a convex surface of the knob fits into a concave surface of the movable unit resulting from the first cavity;
   a main wire inside the stick stretches between a locker and the movable unit, and moves as the movable unit moves;
   the first conic hole and the second conic hole are configured to limit movement of the main wire; and
   at least one affixation hole is located on the slider unit for affixing the proximal part to the proximal radius bone, and at least one affixation hole is on the movable unit for affixing the distal part to the metacarpal bone via affixation wires.

2. The external fixator according to claim 1, wherein, the locker and the knob have a bigger size than a cross section of the slider hole.

3. The external fixator according to claim 1, wherein, at least one joint unit in a form of a truncated sphere has a second cavity and is located between the movable unit and the knob, the convex surface of the knob fits into the concave surface of the joint unit resulting from the second cavity, wherein a convex surface of the joint unit fits into the concave surface of the movable unit.

4. The external fixator according to claim 3, wherein, the joint unit comprises two conic holes.

5. The external fixator according to claim 1, wherein the external fixator further comprises at least one bar, a tulip head and a nut, wherein the at least one bar is located between the tulip head and the nut, for maintaining two fastened parts of a fractured bone in a stable state with both the proximal part and the distal part.

6. The external fixator according to claim 1, wherein, a plurality of rotational adjustment reference holes are located on the stick.

7. The external fixator according to claim 1, wherein the external fixator further comprises the affixation wires, wherein, the affixation wires are threaded Kirschner wires.

8. The external fixator according to claim 1, wherein the external fixator further comprises the affixation wires, wherein, the affixation wires are non-threaded Kirschner wires.

9. The external fixator according to claim 1, wherein the external fixator further comprises the affixation wires, wherein, the affixation wires are tulip heads with nuts.

10. The external fixator according to claim 1, wherein, a rotational fixation screw gets through a rotational fixation hole and touches to the stick for stabilizing the slider unit on the stick on an arranged rotational position.

* * * * *